(12) United States Patent
Singh et al.

(10) Patent No.: US 8,877,816 B2
(45) Date of Patent: Nov. 4, 2014

(54) 4-(OR 5-) SUBSTITUTED CATECHOL DERIVATIVES

(75) Inventors: Jasbir Singh, Naperville, IL (US); Mark E. Gurney, Grand Rapids, MI (US); Alex Burgin, Kingston, WA (US); Vincent Sandanayaka, Northboro, MA (US); Alexander Kiselyov, San Diego, CA (US)

(73) Assignee: Decode Genetics EHF, Reykjavik (IS)

( * ) Notice: Subject to any disclaimer, the term of this patent is extended or adjusted under 35 U.S.C. 154(b) by 223 days.

(21) Appl. No.: 12/275,168

(22) Filed: Nov. 20, 2008

(65) Prior Publication Data
US 2009/0131530 A1   May 21, 2009

Related U.S. Application Data

(60) Provisional application No. 60/989,567, filed on Nov. 21, 2007.

(51) Int. Cl.
| | |
|---|---|
| A61K 31/165 | (2006.01) |
| C07C 233/02 | (2006.01) |
| A61P 29/00 | (2006.01) |
| C07C 311/08 | (2006.01) |
| C07C 275/32 | (2006.01) |
| C07C 43/295 | (2006.01) |
| C07D 213/73 | (2006.01) |
| C07C 45/71 | (2006.01) |
| C07C 43/29 | (2006.01) |
| C07C 205/38 | (2006.01) |
| C07D 213/81 | (2006.01) |
| C07D 213/83 | (2006.01) |

(52) U.S. Cl.
CPC ............ *C07D 213/73* (2013.01); *C07C 311/08* (2013.01); *C07C 275/32* (2013.01); *C07C 43/295* (2013.01); *C07C 45/71* (2013.01); *C07C 43/29* (2013.01); *C07C 205/38* (2013.01); *C07D 213/81* (2013.01); *C07D 213/83* (2013.01)
USPC ............. 514/619; 564/188; 564/32; 568/586; 546/315; 546/311; 546/309; 558/414; 558/418

(58) Field of Classification Search
None
See application file for complete search history.

(56) References Cited

U.S. PATENT DOCUMENTS

| | | | |
|---|---|---|---|
| 6,245,774 B1 | 6/2001 | Warrellow et al. | |
| 7,189,718 B2 | 3/2007 | Dunn et al. | |
| 2003/0149052 A1* | 8/2003 | Schumacher et al. | ... 514/255.05 |
| 2004/0198736 A1* | 10/2004 | Dunn et al. | ................ 514/247 |
| 2006/0046980 A1 | 3/2006 | Erion et al. | |
| 2006/0100218 A1* | 5/2006 | Ibrahim et al. | ................ 514/256 |
| 2006/0223874 A1 | 10/2006 | Martin et al. | |
| 2007/0105852 A1* | 5/2007 | Castano Mansanet et al. | ........................ 514/231.5 |
| 2008/0045511 A1* | 2/2008 | Kennedy-Smith et al. | ... 514/220 |

FOREIGN PATENT DOCUMENTS

| | | | | |
|---|---|---|---|---|
| WO | 94/12461 | 6/1994 | | |
| WO | 95/35283 | 12/1995 | | |
| WO | WO 99/23076 | * 5/1999 | ........... | C07D 231/56 |
| WO | 01/85670 | 11/2001 | | |
| WO | 02/094319 | 11/2002 | | |
| WO | 03/074055 | 9/2003 | | |
| WO | 2006/128056 | 11/2006 | | |
| WO | 2006/128058 | 11/2006 | | |

OTHER PUBLICATIONS

Silverman, The Organic Chemistry of Drug Design and Drug Action, 1992, pp. 15-20.*
ZCAPLUS abstract of WO 01/85670, published Nov. 15, 2001.*
Dhamija et al. In the International Journal of Stroke, vol. 7, Issue 7, 2012, 4 pages.*
DeMarch et al., Neurobiology of Disease, vol. 30 (2008), pp. 375-387.*
Park et al. , Arch. Pharm. Res. vol. 30, No. 4, 2007, pp. 486-492.*
DrugBank (http://www.drugbank.ca/drugs/DB0113, Jun. 2005, 8 pages.*
Haynes et al. (Journal of Pharmaceutical Sciences, Oct. 2005, vol. 94, No. 10, pp. 2111-2120.*
Factor et al., The chemistry of γ-irradiated bisphenol-A polycarbonate, Polymer Degradation and Stability (1994), 45(1), pp. 127-137.
Calas et al., Synthesis of new trimethoprim analogs. Antibacterial structure-activity relationship, European Journal of Medicinal Chemistry (1982), 17(6), pp. 497-504 (in French—no translation).
Calas et al., New 2,4-diamino-5-arylmethylpyrimidines. Study of the relation between structure and antibacterial activity, European Journal of Medicinal Chemistry (1979), 14(6), pp. 529-537 (in French—no translation).
Maier et al., Seven imidazole alkaloids from Lepidium sativum, Phytochemistry (1998), 49(6), 1791-1795.

(Continued)

*Primary Examiner* — Rosalynd Keys
(74) *Attorney, Agent, or Firm* — Heslin Rothenberg Farley & Mesiti P.C.

(57) ABSTRACT

Compounds of the formula:

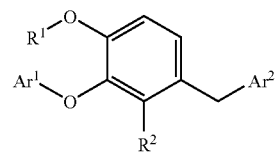

are disclosed. The compounds act as phosphodiesterase-4 modulators, and useful for treating stroke, myocardial infarct, and cardiovascular inflammatory conditions. Other embodiments are also disclosed.

29 Claims, No Drawings

(56) References Cited

OTHER PUBLICATIONS

International Search Report and Written Opinion for PCT/US2008/084188, Feb. 2009.

Smith, et al., "Reissert compound chemistry. XXVI. The synthesis of bis(benzylisoquinolines)", Journal of Heterocyclic Chmistry, 13(3), pp. 573-576 (1976), June.

Knabe, et al., "[Biological activities of phaeantharine chloride and some synthetic intermediates]", Archiv Der Pharmazie Jan. 1988, vol. 321, Nr. 1, pp. 35-36 (1988) (in German, no translation).

Knabe, et al., "A further synthesis of phaeantharine", Archiv Der Pharmazie 1986 De, vol. 319, No. 10, pp. 950-952 (1986) (in German, no translation).

Knabe, et al., "Totalsynthese des Phaeantharins", Archiv Der Pharmazie 1984 DE, vol. 317, pp. 9294, (1984) (in German, no translation).

Anderson et al., "Oxidation of Phenois. Part I. A Study of the Oxidation of O-Cresol and Other O-Alkylphenols", Journal of Chemical Research. Miniprint, Scientific Reviews, Jan. 1, 1977, pp. 201-231, (1997).

Popp et al., "Reissert Compound Studies. XII. Synthesis of O-Methyldauricine", Journal of Organic Chemistry, American Chemical Society, Easton, vol. 31., No. 7, pp. 2296-2299 (1966).

International Preliminary Report on Patentability and Written Opinion of the International Searching Authority, received in connection with PCT/US2008/084188, May 2010.

* cited by examiner

4-(OR 5-) SUBSTITUTED CATECHOL DERIVATIVES

CROSS-REFERENCE TO RELATED APPLICATIONS

This application claims priority from U.S. provisional application 60/989,567, filed Nov. 21, 2007, the entire disclosure of which is incorporated herein by reference. The application is related to, but does not claim priority from, four other US non-provisional applications filed of even date herewith and having Jasbir Singh as a common inventor. The applications are titled "BIARYL PDE4 INHIBITORS FOR TREATING INFLAMMATORY, CARDIOVASCULAR AND CNS DISORDERS", "BIARYL PDE4 INHIBITORS FOR TREATING PULMONARY AND CARDIOVASCULAR DISORDERS", "SUBSTITUTED BENZOAZOLE PDE4 INHIBITORS FOR TREATING PULMONARY AND CARDIOVASCULAR DISORDERS" and "SUBSTITUTED BENZOAZOLE PDE4 INHIBITORS FOR TREATING INFLAMMATORY, CARDIOVASCULAR AND CNS DISORDERS". Their disclosures are incorporated herein by reference.

FIELD OF THE INVENTION

The invention relates to 4-substituted or 5-substituted catechol derivatives that are useful for treating stroke, myocardial infarct, and cardiovascular inflammatory conditions, to pharmaceutical compositions comprising these compounds, and to methods for the treatment of stroke, myocardial infarct, and cardiovascular inflammatory conditions in a mammal.

BACKGROUND OF THE INVENTION

PDE4 is the major cAMP-metabolizing enzyme found in inflammatory and immune cells. PDE4 inhibitors have proven potential as anti-inflammatory drugs, especially in inflammatory pulmonary diseases such as asthma, COPD and rhinitis. They suppress the release of cytokines and other inflammatory signals and inhibit the production of reactive oxygen species. A large number of PDE4 inhibitors have been developed for a variety of clinical indications (Torphy and Page. 2000. TIPS 21, 157-159; Burnouf and Pruniaux. 2002. Curr. Pharm. Design 8, 1255-1296; Lipworth. 2005. Lancet 365, 167-175). To quote from a recent article in the British Journal of Pharmacology, "PDE4 inhibitors have been in development as a novel anti-inflammatory therapy since the 1980s with asthma and chronic obstructive pulmonary disease (COPD) being primary indications. Despite initial optimism, none have yet reached the market. In most cases, the development of PDE4 inhibitors of various structural classes, including cilomilast, filaminast, lirimilast, piclamilast, tofimilast . . . has been discontinued due to lack of efficacy. A primary problem is the low therapeutic ratio of these compounds, which severely limits the dose that can be given. Indeed, for many of these compounds it is likely that the maximum tolerated dose is either sub-therapeutic or at the very bottom of the efficacy dose-response curve. Therefore, the challenge is to overcome this limitation." [Giembycz, Brit. J. Pharmacol. 155, 288-290 (2008)]. Many of the PDE4 inhibitors of the prior art have not reached the market because of the adverse side effect of emesis (Giembycz 2005. Curr. Opin. Pharm. 5, 238-244). Analysis of all known PDE4 inhibitors suggests that they are competitive with cAMP and bind within the active site (Houslay et al. 2005. DDT 10, 1503-1519); this may explain their narrow therapeutic ratio.

The compounds of the present invention are non-competitive inhibitors of cAMP while being gene-specific inhibitors (PDE4D), and, based on the target rationale and in vitro potency, a person of skill in the art would expect the compounds to be useful as anti-inflammatory agents for the treatment, amelioration or prevention of inflammatory diseases and of complications arising therefrom.

SUMMARY OF THE INVENTION

In one aspect, the invention relates to a compound of formula I:

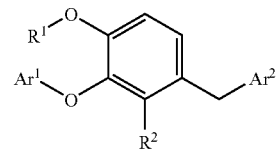

wherein
$R^1$ is chosen from H, $(C_1-C_8)$alkyl and halo$(C_1-C_8)$alkyl;
$R^2$ is chosen from H and halo;
$Ar^1$ is selected from optionally substituted phenyl and optionally substituted heteroaryl; and
$Ar^2$ is selected from substituted phenyl and substituted heteroaryl.

In another aspect, the invention relates to pharmaceutical compositions comprising a pharmaceutically acceptable carrier and a compound as described above.

In a third aspect, the invention relates to methods for the treatment or prophylaxis of a disease or condition mediated by phosphodiesterase-4. The methods comprise administering to a mammal a therapeutically effective amount of a compound having the general formula I. The disease or condition may be related to allergic, acute or chronic inflammation. The disease may be, for example, atherosclerosis, thrombosis, stroke, acute coronary syndrome, stable angina, peripheral vascular disease, critical leg ischemia, intermittent claudication, abdominal aortic aneurysm or myocardial infarction.

Selective PDE4 inhibitors of the invention are useful in improving cognition and thus useful for treating learning disorders, memory loss and other cognitive dysfunctions. Selective PDE4 inhibitors of the invention are also useful for treating asthma and Chronic Obstructive Pulmonary Disease (COPD). Compounds of the invention, which inhibit tumor growth and metastases, also find utility in the treatment and prevention of cancer, including esophageal cancer, brain cancer, pancreatic cancer, and colon cancer.

DETAILED DESCRIPTION OF THE INVENTION

In composition aspect, the invention relates to compounds of formula I:

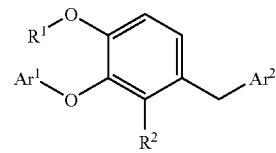

In accordance with some embodiments of the invention, $Ar^1$ is selected from optionally substituted phenyl and optionally substituted monocyclic heteroaryl. For example, $Ar^1$ may be selected from: (a) phenyl; (b) phenyl substituted in the meta or para position with a single substituent; and (c) pyridinyl. In accordance with some embodiments, $Ar^1$ is phenyl substituted in the meta or para position with a group chosen from halogen, nitro, cyano, fluoromethyl and amino. (Fluoromethyl is intended to include $CHF_2$, $CH_2F$ and $CF_3$.)

In accordance with some embodiments, $Ar^2$ is selected from substituted phenyl and substituted monocyclic heteroaryl. For example, $Ar^2$ may be selected from: (a) phenyl substituted in the para position with a single substituent; and (b) pyridinyl substituted in the para position with a single substituent. In accordance with some embodiments, $Ar^2$ is phenyl substituted in the para position with a group chosen from halogen, nitro, cyano, urea, alkylurea, hydroxy, alkylsulfonylamino, amino, haloalkyl, loweralkoxy, carboxy, alkoxycarbonyl, alkylaminocarbonyl, alkylamino, dialkylamino, mercapto, alkylthio, alkylsulfoxide, alkylsulfone, acylamino, phenyl and benzyl. In other embodiments, $Ar^2$ is 3-pyridinyl substituted in the 6-position with a group chosen from halogen, nitro, cyano, urea, sulfonylurea, hydroxy, alkylsulfonylamino, amino, haloalkyl, loweralkoxy, carboxy, alkoxycarbonyl, alkylaminocarbonyl, alkylamino, dialkylamino, mercapto, alkylthio, alkylsulfoxide, alkylsulfone, acylamino, phenyl and benzyl. For example, $Ar^2$ may be 3-pyridinyl substituted in the 6-position with a group chosen from nitro, urea, sulfonylurea, alkylsulfonylamino, amino, alkylamino, dialkylamino and acylamino.

In accordance with some embodiments of the invention, $R^2$ is hydrogen. In accordance with other embodiments, $R^2$ is fluorine.

In accordance with some embodiments of the invention, $R^1$ is hydrogen. In accordance with other embodiments, $R^1$ is methyl.

In some embodiments of the invention, the compound is selected from any of the species set forth below.

There is also provided, in accordance with embodiments of the invention, a pharmaceutical composition comprising a compound of formula I and a pharmaceutically acceptable carrier, excipient or diluent therefore.

All of the compounds falling within the foregoing parent genus I and its subgenera are useful as PDE4 inhibitors. In addition to the novel compounds, certain known species fall within the genus I, although no utility in inhibiting PDE4 has been suggested for these species. It may be found upon examination that compounds that have been excluded from the claims to compounds or compounds that have been excluded from the claims to methods are patentable to the inventors in this application; it may also be found that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all compounds of formula I except those that are in the public's possession. In particular, a search of the literature indicates that, when $R^1$ and $R^2$ are both H, compounds in which $Ar^2$ is 2,6-disubstituted phenyl are known, and when $R^1$ is $CH_3$ and $R^2$ is H, compounds in which $Ar^2$ is 2,4-diaminopyrimidin-5-yl are known.

Throughout this specification the terms and substituents retain their definitions.

Alkyl is intended to include linear, branched, or cyclic hydrocarbon structures and combinations thereof. A combination would be, for example, cyclopropylmethyl. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

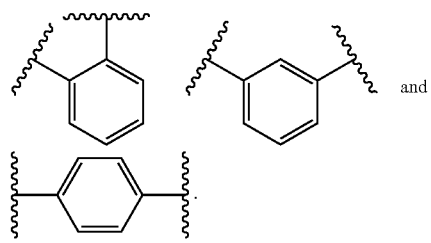

and

Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus $(C_3-C_{10})$ carbocycle refers to such systems as cyclopropane, benzene and cyclohexene; $(C_8-C_{12})$ carbopolycycle refers to such systems as norbornane, decalin, indane and naphthalene. Carbocycle, not otherwise limited, refers to monocycles, bicycles and polycycles.

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

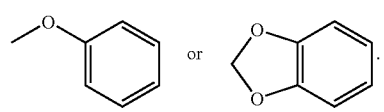

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). It does not refer to doubly bonded oxygen, as would be found in carbonyl groups. Similarly, thiaalkyl and azaalkyl refer to alkyl residues in which one or more carbons have been replaced by sulfur or nitrogen, respectively. Examples include ethylaminoethyl and methylthiopropyl.

Acyl refers to formyl and to groups of 1, 2, 3, 4, 5, 6, 7 and 8 carbon atoms of a straight, branched or cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, propionyl, isobutyryl, t-butoxycarbonyl, benzoyl, benzyloxycarbonyl and the like. Lower-acyl refers to groups containing one to four carbons. The double bonded oxygen, when referred to as a substituent itself, is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. For the purposes of the present invention, heteroaryl does not encompass such ambiguous species as oxoheterocycles and partially saturated polycyclic heterocycles. For example, pyridine, thiazole, quinoline, pyrimidine, pyridazine and pyrazole are heteroaryl; pyridone, thiazolone, quinolone, tetrahydroquinoline, pyrimidinone, pyridazinone and pyrazolone are not heteroaryl. For the purposes of the present invention, it is preferred that the heteroaryl substituent be monocyclic or bicyclic.

Arylalkyl refers to a substituent in which an aryl residue is attached to the parent structure through alkyl. Examples are benzyl, phenethyl and the like. This is in contradistinction to alkylaryl, in which an aryl residue is attached to the parent structure and is itself substituted with an alkyl (e.g. a p-tolyl residue). Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

The term "heterocycle" means a monocyclic, bicyclic or tricyclic residue with 1 to 13 carbon atoms and 1 to 4 heteroatoms chosen from the group consisting of nitrogen, oxygen and sulfur. The nitrogen and sulfur heteroatoms may optionally be oxidized, and the nitrogen heteroatom may optionally be quaternized. Unless otherwise specified, a heterocycle may be non-aromatic or aromatic. The heterocycle may be fused to an aromatic hydrocarbon radical. Suitable examples of heterocycles include pyrrolidine, pyrazole, pyrrole, indole, 2-pyrrolinyl, 3-pyrrolinyl, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic; examples include pyridine, pyrrole and thiazole. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, 1,3-dioxolanyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, 1,4-dithianyl, 1,3,5-triazinyl, 1,2,5-trithianyl, benzo(b)thiophenyl thiadiazolyl, benzopyranyl, benzothiazolyl, tetrahydrofuryl, pyranyl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl. For the purpose of the present disclosure, heteroaryl includes the corresponding oxo compounds. e.g. pyridinone, imidazolone, pyridazinone, pyrimidinone etc.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine.

As used herein, the term "optionally substituted" may be used interchangeably with "unsubstituted or substituted". Substituted alkyl, aryl, cycloalkyl, heterocyclyl, etc. refer to alkyl, aryl, cycloalkyl, or heterocyclyl wherein up to three H atoms in each residue are replaced with a specified radical. For example, substituted alkyl, aryl, cycloalkyl, heterocyclyl etc. refer to alkyl, aryl, cycloalkyl, or heterocyclyl wherein up to three one or more H atoms in each residue are replaced with halogen, alkyl, haloalkyl, haloalkoxy, hydroxy, loweralkoxy (which for the purpose of the present disclosure includes methylene dioxy and ethylene dioxy), oxaalkyl, carboxy, carboalkoxy (also referred to as alkoxycarbonyl [—C(=O)O-alkyl]), carboxamido ([—C(=O)NH$_2$]), alkylaminocarbonyl [—C(=O)NH-alkyl]), alkoxycarbonylamino [HNC(=O)O-alkyl], acyl, alkoxyalkyl, benzenesulfonyl, cyano, carbonyl, nitro, amino, hydroxyalkyl, alkylamino, dialkylamino, aminoalkyl, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, alkoxycarbonylamino, acetoxy, sulfoxide, sulfone, sulfonylamino, aryl, phenyl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, or heteroaryloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. Additional substituents that are considered within the scope of the term are: —NH(tBoc), —CHO, —NHSO$_2$NH$_2$, —C(=O)NH$_2$, —CH$_2$NH$_2$, —CH$_2$OH, —CH$_2$CH$_2$OH and —SO$_2$NH$_2$ The term "halogen" means fluorine, chlorine, bromine or iodine.

Haloakyl refers to an alkyl group in which one or more hydrogens are replaced by halogen, for example, trifluoromethyl, trifluoromethoxy, trichloroethyl, and difluoromethyl. The term "haloalkoxy" means alkoxy substituted with one or more halogen atoms. The terms "alkylcarbonyl" and "alkoxycarbonyl" mean —C(=O)alkyl or —C(=O)alkoxy, respectively. Fluoroalkyl refers to an alkyl wherein one or more hydrogens are replaced by a corresponding number of fluorines. For instance, fluoromethyl can refer to a methyl group substituent having one, two or three fluorines attached.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

Substituents R″ are generally defined when introduced and retain that definition throughout the specification and in all independent claims.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2$H, $^3$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Compounds that contain isotopes $^{11}$C, $^{13}$N, $^{15}$O and $^{18}$F are well suited for positron emission tomography. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with disorders or conditions mediated by phosphodiesterase-4. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

As used herein, and as would be understood by the person of skill in the art, the recitation of "a compound" is intended to include salts, solvates and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. In accordance with some embodiments of the invention, the salt is a hydrochloride salt.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. Inclusion complexes are described in Remington: The Science and Practice of Pharmacy 19$^{th}$ Ed. (1995) volume 1, page 176-177. The most commonly employed inclusion complexes are those with cyclodextrins, and all cyclodextrin complexes, natural and synthetic, with or without added additives and polymer(s), such as described in U.S. Pat. Nos. 5,324,718 and 5,472,954, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, carbonic, citric, ethanedisulfonic, ethanesulfonic, ethylene-diaminetetraacetic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, pamoic, pantothenic, phosphoric, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine.

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations," is incorporated herein by reference.

PDE4 inhibitors have been shown to be effective therapeutic agents in clinical studies. For example, administration of cilomilast and roflumilast (PDE4 inhibitors) to patients suffering from asthma and COPD showed initially excellent results, although the effect of cilomilast disappeared on long-term trial [Lipworth, *Lancet* 365, 167-175 (2005)]. Genetic studies have clearly demonstrated an association between PDE4D and ischemic stroke (Gretarsdottir et al. 2003. Nature Genetics. 35, 1-8). L-454,560, a selective PDE4 inhibitor has been shown to improve learning in a rat model in vivo [Huang et al. *Biochemical Pharmacology* 73, 1971-1981 (2007)]. This suggests that selective PDE4 inhibitors will be useful in treating learning disorders, memory loss (e.g. Alzheimer's disease) and other cognitive dysfunctions. Rolipram, another selective PDE4 inhibitor, has been shown to enhance cognition in multiple rodent models [Blokland et al., Current Pharmaceutical Design 12, 2511-2523 (2006)] as well as in primates [Rutten et al., 2008, Psychopharmacology 196, 643-648 (2008)]. Rolipram also improves the outcome in two separate studies in mice in vivo in models accepted by persons of skill in the art as predictive of utility in schizophrenia [Kanes et al., *Neuroscience* 144, 239-246 (2007); Davis and Gould, *Behav. Neurosci.* 119, 595-602 (2005)]. Rolipram has also been shown to exhibit a neuroprotective effect in a rat model of Huntington's disease [DeMarch et al. Neurobiol. Dis. 25, 266-273 (2007)]. This suggests that PDE4 modulators will be useful for treating many CNS disorders. Selective PDE4 inhibitors (e.g. rolipram) are also useful for treating bone loss [Yao et al., *J. Musculoskelet. Neuronal Interact.* 7, 119-130 (2007)].

Additionally, a PDE4 inhibitor, YM976, was shown to ameliorate the effects of experimentally-induced interstitial cystitis in rats, resulting in a decrease in the frequency of urination and an increase in the volume of urine at each time of urination [Kitta et al., *BJU Int.* 102, 1472-1476 (2008)]. Another PDE4 inhibitor, IC485, was shown to be equally efficacious as tolteradine tartrate, a marketed drug for treating overactive bladder, in a rodent model of obstructive bladder [Kaiho et al. BJU Int. 101, 615-20 (2008)]. These findings suggest that PDE4 inhibitors will be useful in treating symptoms of bladder inflammation, such as overactivity and pain.

In addition to the foregoing studies demonstrating utility in in vivo models, a number of authors have suggested connections between PDE4 inhibition and putative utilities as antidepressants [Houslay et al., Drug Discov Today 10, 1503-1519 (2005); Polesskaya et al., Biol. Psychiatr. 61, 56-64 (2007); anon. *Current Opin. Invetig. Drugs* 5, 34-39 (2004)] and as anxiolytics [Zhang et al., *Neuropsychopharmacology* Aug. 15, 2007 Epub; Chemy et al., *Biochim. Biophys. Acta* 1518, 27-35 (2001)]. Rolipram has been shown in human clinical trials to ameliorate depression [Hebenstreit et al., Pharmacopsychiat. 22, 156-160 (1989)]. Other possible utilities may include Pick's disease and epilepsy.

Furthermore, the compounds, compositions and methods of the present invention are useful in treating cancer. Phosphodiesterase activity has been shown to be associated with hematological malignancies [Lerner et al., *Biochem. J.* 393, 21-41 (2006); Ogawa et al., *Blood* 99, 3390-3397 (2002)].

Furthermore, the compounds, compositions and methods of the present invention, particularly when radiolabeled as described above or labeled by methods well-known in the art with florescent and spin labels, may be employed as imaging agents and in other ways for diagnosis and/or treatment. Moreover, immobilization of compounds of the invention on solid support could be of utility for affinity purification and modification of compounds of the invention with chemically active groups may be used for protein labeling.

For many of the utilities outlined above, it may be advantageous to administer compounds of the general formula I together with cholinesterase inhibitors (e.g. tacrine, huperzine, donepezil); NMDA antagonists (e.g. lanicemine, remacemide, neramexane, memantine); calpain inhibitors (e.g. CEP-3122); antioxidants (e.g. vitamin E, coenzyme Q10) and agents that have shown clinical efficacy but whose mechanism is unclear (e.g. dimebon). Compounds of formula I may also be administered together with one or more of the following agents to improve cognition: amisulpride, atomoxetine, bromocryptine, buspirone, caffeine, chlorpromazine, clonidine, clozapine, diazepam, flumazenil, fluoxetine, galantamine, guanfacine, methylphenidate, idazoxan, modafinil, olanzapine, paroxetine, pergolide, phenserine, quetiapine, risperidone, rivastigmine, SGS742 and sulpiride.

The cognitive impairment to be treated may arise from one or more of the following disorders, which may not in themselves be necessarily associated with PDE4 abnormality: acute pain, AD/HD—Attention deficit hyperactivity disorder, AIDS dementia complex, alcoholism, amphetamine addiction, amygdalo-hippocampectomy, anorexia nervosa, anterior parietal damage, antisocial behavior, antisocial personality disorder, anxiety, autism, basal ganglia lesions, bipolar disorder, borderline personality disorder, camptocormia, capgras syndrome, carcinoid syndrome, carotid endarterectomy surgery, chronic drug misuse, chronic fatigue syndrome, chronic occupational solvent encephalopathy, chronic pain, brain ischemia, coronary artery bypass surgery, critical illness requiring intensive care, dementia Alzheimer-type (DAT), dementia Lewy Body type, dementia of frontal type, dementia caused by ischemia, dental pain, developmental dyslexia, diabetes, dorsolateral frontal cortical compression, Down's Syndrome, drug abuse, dysexecutive syndrome, fibromyalgia, frontal lobe damage, frontal lobe excision, frontal variant frontotemporal dementia, gluten ataxia, hallucinosis, head injury, hearing loss, heart disease, heart failure, heavy social drinking, hepatic encephalopathy, heroin addiction, herpes encephalitis, hippocampal atrophy, HIV/AIDS, Huntington's disease, hydrocephalus, hypercortisolemia, hyperostosis frontalis internal hypertension, idiopathic pain, insomnia, Korsakoff syndrome, late paraphrenia, lead exposure, left ventricular systolic dysfunction, orbitofrontal cortex lesion, liver failure, long term health effects of diving, Machado-Joseph disease, mad hatter's disease, manic depression, melancholia, mercury poisoning, mild cognitive impairment (MCI), mild cognitive impairment (MCI) of aging, motor neuron disease, multiple sclerosis, multiple system atrophy, narcolepsy, neuronal migration disorders, normal pressure hydrocephalus, obsessive compulsive disorder, organophosphate pesticide exposure, panic disorder, paraphrenia, Parkinson's disease, periventricular brain insult, personality disorder, gasoline sniffing, phenylketonuria, postconcussion syndrome, premature birth needing intensive care, premenstrual dysphoric disorder, progressive supranuclear palsy, psychopathy, psychosis, questionable dementia, renal cancer, Roifman syndrome, schizoaffective disorder, schizophrenia, seasonal affective disorder, self harm, semantic dementia, specific language impairment, social withdrawal in schizophrenia, solvent encephalopathy, spina bifida, Steele-Richardson-Olzsewski syndrome, stiff person syndrome, striatocapsular infarct, subarachnoid hemorrhage, substance abuse, tardive dyskinesia, temporal lobe excision, temporal lobe lesion, tinnitus, Tourette's syndrome, transient cerebral ischemia, traumatic brain injury, trichotillomania, tuberous sclerosis, and white matter lesions.

While it may be possible for compounds of formula I to be administered as the raw chemical, it will often be preferable to present them as part of a pharmaceutical composition. In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, 20$^{th}$ Edition, 2000. The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. Nos. 5,230,884, 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining compounds of formula I are presented below. Other compounds of formula I may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Below are specific examples.

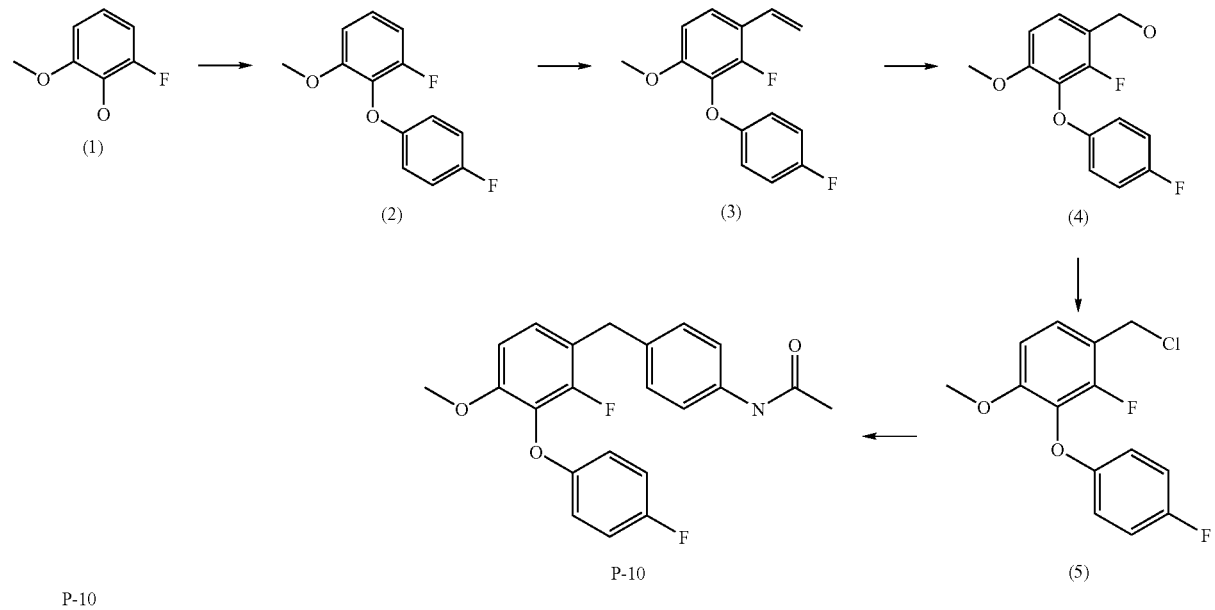

Scheme 1.

1-Fluoro-2-(4-fluoro-phenoxy)-3-Methoxy benzene (2). To a suspension of 2-fluoro-6-methoxy phenol (1) (2.8 g, 20 mmol), N,N-dimethyl glycine.HCl (837 mg, 6 mmol), $Cs_2CO_3$ (13 g, 40 mmol), 1-fluoro-4-iodobenzene (2.3 mL, 20 mmol), in Dioxane (40 ml) was added copper iodone (381 mg, 2 mmol). The reaction mixture was stirred at 105° C. over 1 week. Upon heating the reaction mixture turned from brown to a bright green. After cooling to room temperature, the reaction mixture was filtered and the filtrate was concentrated in-vacuo. The crude was purified by silica gel eluted with hexane/EtOAc (10:1), concentrated in-vacuo, to provide 300 g (21% yield) of product (2).

4-Fluoro-3-(4-fluoro-phenoxy)-4-Methoxy benzaldehyd (3). A flask was charged with compound (2) (300 mg, 1.27 mmol), dichlromethyl methyl ether (0.11 mL, 1.27 mmol) and DCM (5 mL). The reaction mixture was immersed in an ice bath and titanium chloride (1 mL, 6.35 mmol) was added to the mixture dropwise (5 minute period). The red reaction mixture was stirred overnight at room temperature. After overnight stirring the reaction mixture was carefully poured into a beaker containing ice water. The mixture was stirred for 30 min. Then it was poured into a separatory funnel and was extracted with DCM (2×10 mL). The organic layers were washed with aq. sat. NaHCO₃ solution. The organic layer was collected, dried over Na₂SO₄ and concentrated in-vacuo. Crude material 300 mg, (3) was used as such for the subsequent reaction.

[2-Fluoro-3-(4-fluoro-phenoxy)-4-methoxy-phenyl]-methanol (4). A round bottom was charged with benzaldehyde (3) (1.1 mol, 300 mg), ethanol (10 mL) and NaBH₄ (5.5 mmol, 208 mg). The white reaction mixture was stirred at room temperature for 4 h. To the reaction mixture water (25 mL) was added and the mixture was stirred for 10 minutes. The mixture was extracted with EtOAc (2×25 mL). The combined organic layers were washed with brine, dried over Na₂SO₄ and concentrated in-vacuo to provide (4) 250 mg, (85% yield). ¹H-NMR (400 MHz, DMSO-d₆).

1-Chloromethyl-2-fluoro-3-(4-fluoro-phenoxy)-4-methoxy-benzene (5). A solution of the benzyl alcohol (4) (250 mg, 0.94 mmol) in toluene (4 mL) was put in one side of the U-tube, in which carbon tetrachloride (12 mL) was placed, and SOCl₂ (0.12 mL) was put into the other side of the U-tube. The mixture was gently stirred at rt. The SOCl₂ layer vanished after 3 h. The reaction progress was monitored by TLC analysis. After the reaction was completed (4 h), the toluene layer was decanted and poured into water (30 mL). The mixture was extracted with ether (30 mL), washed with brine and dried over Na₂SO₄. The residue was purified by silica gel column chromatography, eluted with hexane:EtOAc (5:1). The volatile material was removed under reduced pressure to give 258 mg (96% yield) of desired the product (5) as pale yellow oil. ¹H-NMR (400 MHz, DMSO-d₆).

N-{4-[2-Fluoro-3-(4-fluoro-phenoxy)-4-methoxy-benzyl]-phenyl}-acetamide P-10. A vial was charged benzyl chloride (5) (258 mg, 0.9 mmol), 4-acetoamide phenyl boronic acid (197 mg, 1.1 mmol) and DME (10 mL). A solution of sodium carbonate in water (1M, 2.7 mmol, 2.7 mL) was added to the reaction mixture. The reaction was degassed with N₂. Then the palladium tetrakis (52 mg, 0.045 mmol) was added and the reaction mixture was stirred and heated at 85° C. for 4 h. Then the reaction mixture was cooled to rt and diluted with EtOAc (30 mL). The reaction mixture was washed with water (30 mL), brine, and dried over Na₂SO₄. The residue was purified by silica gel column chromatography, eluted with DCM:MeOH (100:2). The volatile material was removed under reduced pressure to give 29.5 mg (8% yield) of desired product P-10 as pale white solid. ¹H-NMR (400 MHz, CDCl₃). LCMS: 97%.

Scheme 2:

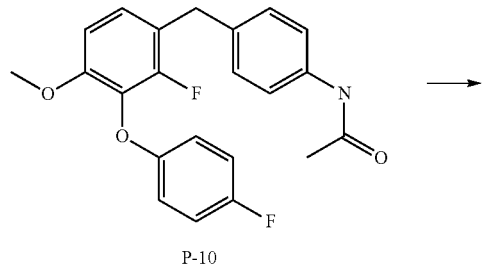

P-10

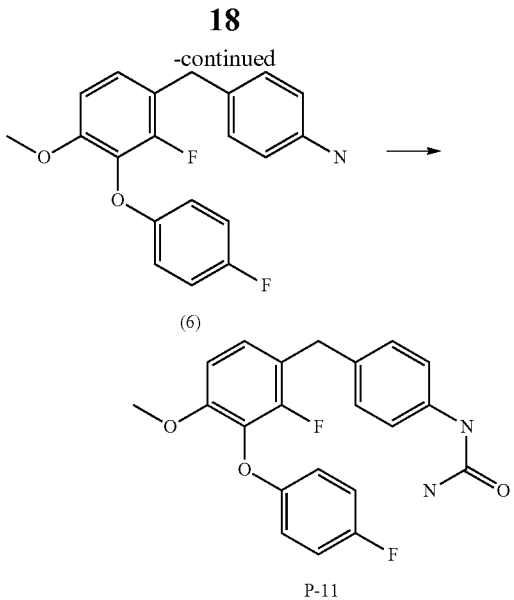

{4-[2-Fluoro-3-(4-fluoro-phenoxy)-4-methoxy-benzyl]-phenyl}-urea P-11. A vial was charged P-10 (0.05 mmol, 20 mg), ethanol (2 mL) and HCl (12N, 0.5 mmol, 0.042 mL). Then the reaction mixture was stirred and heated at 85° C. After overnight stirring the reaction mixture was cooled to rt and then the solvent was removed leaving a white solid (6) that was used as such for the next step. To the white solid (6), sodium cyanide (0.4 mmol, 26 mg) was added. Then an acetic acid/water (2:1, 2 mL) solution was added and the homogeneous mixture was stirred at rt for 30 min. and then at 80° C. for 4 h. The reaction mixture was cooled to rt and water (10 mL) was added. A white solid precipitated out. The solid was collected and dried to give 7.5 mg (39% yield) of desired product P-11. ¹H-NMR (400 MHz, DMSO-d₆). LCMS: 99%.

Scheme 4:

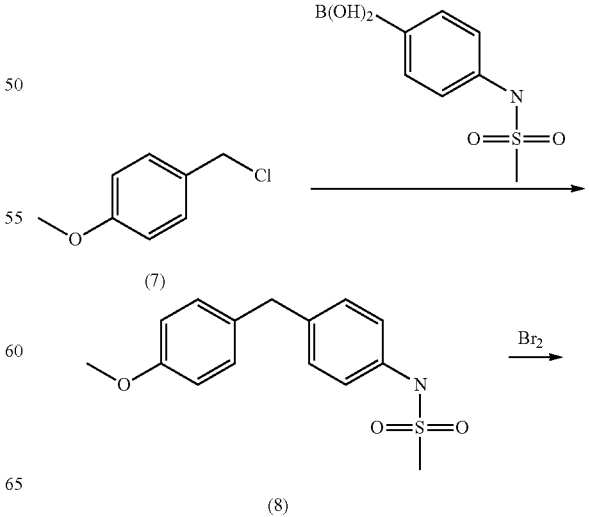

-continued

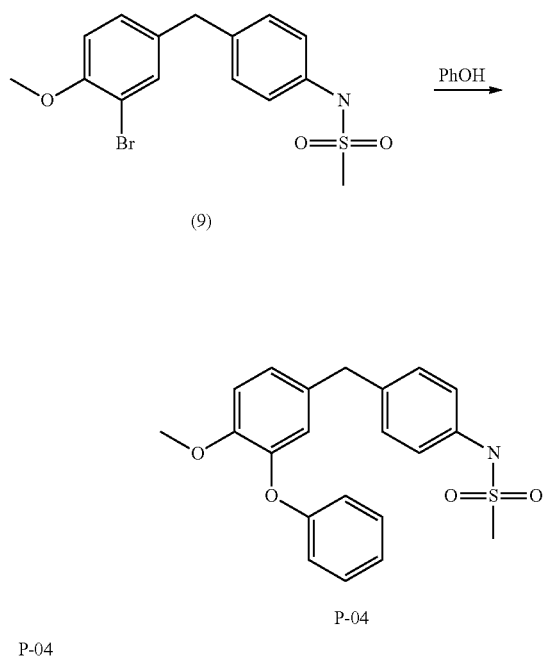

N-[4-(4-Methoxy-benzyl)-phenyl]-methanesulfonamide (8). A round bottom was charged with 4-methanesulfonamide phenyl boronic acid (6.5 mmol), Pd(OAc)$_2$ (0.5 mmol, 112 mg), PPh$_3$ (μmol, 262 mg), K$_2$CO$_3$ (7.5 mmo, 1.03 g), DME (50 mL), water (5 mL), ethanol (5 mL) and 4-methoxy benzyl chloride (7). The reaction mixture was immersed in a 90° C. bath and was stirred under N$_2$ for 48 h. Then the reaction was cooled to rt and poured into a beaker with water (100 mL). A cream solid precipitated out. The solid was collected and purified by flash silica gel column chromatography. The column was eluted with hexane/EtOAc (2:1) to give compound (8) 1.4 g (96% yield) as a white solid.

N-[4-(3-Bromo-4-methoxy-benzyl)-phenyl]-methanesulfonamide (9). A round bottom was charged with N-[4-(4-Methoxy-benzyl)-phenyl]-methane sulfonamide (8) (1.4 g, 4.8 mmol), acetic acid (15 mL) and slow addition of bromine (5 minute period, 0.23 mL, 5.2 mmol). The reaction mixture was stirred at room temperature overnight. To the yellow homogeneous reaction mixture 15% w/v of aq. NaHSO$_3$ (50 mL) was added. The reaction mixture formed a white precipitate. The reaction mixture was stirred for 30 minutes. Then the solid was collected, rinsed several times with water and dried in vacuo to provide 961.9 mg (56% yield) of product (9).

N-[4-(4-Methoxy-3-phenoxy-benzyl)-phenyl]-methanesulfonamide P-04. A round bottom was charged with Cs$_2$CO$_3$ (736 mg, 2.26 mmol), phenol (212 mg, 2.26 mmol) and NMP (2 mL). Then (9) (418 mg, 1.13 mmol) was added followed by TMHD (0.022 mL, 0.11 mmol) and CuCl (55 mg, 0.56 mmol). The reaction mixture was stirred at 120° C. for 24 h. Then the reaction was cooled to rt and concentrated in-vacuo. The crude was purified by flash silica gel column chromatography. The column was eluted with hexane/EtOAc (2:1) to give 121.2 mg (28% yield) of P-04. LCMS: 99%.

Scheme 5

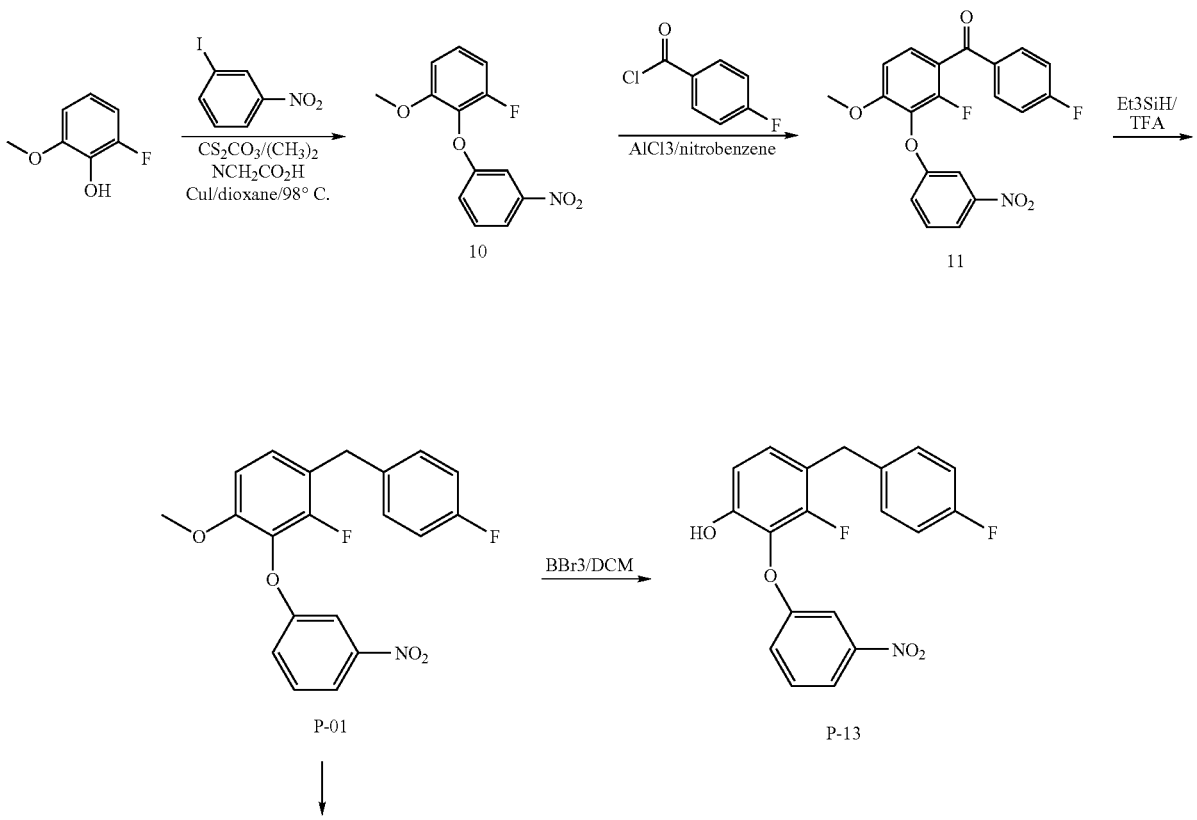

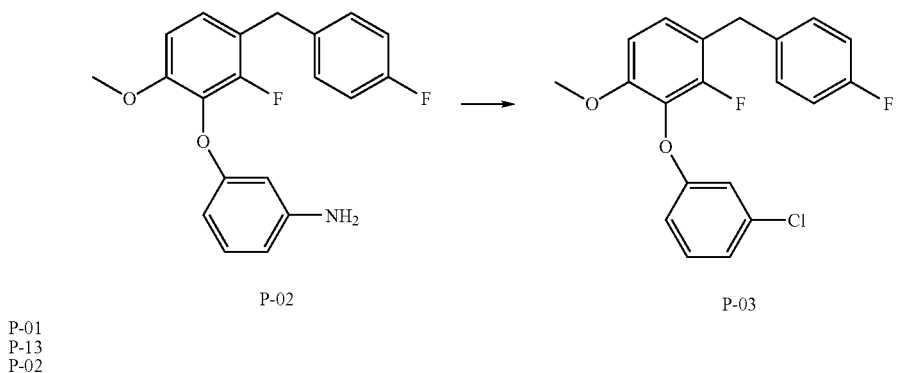

P-01
P-13
P-02
P-03

1-Fluoro-3-methoxy-2-(3-nitro-phenoxy)-benzene (10). To a 250 mL pressure resistant vial which contained a mixture of 2-fluoro-6-methoxy-phenol (1000 mg, 7 mmole), 1-iodo-3-nitro-benzene (2500 mg, 10 mmole), $Cs_2CO_3$ (1200 mg, 7 mmole) and N,N-dimethylglycine.HCl (200 mg, 1.5 mmole) in dioxane (40 mL) was added CuI (140 mg, 0.7 mmole) at rt. The reaction mixture was bumbled with Ar for 5 min at rt and then the vial was sealed. The reaction mixture was stirred and heated to 98° C. for 5 d. After cooling to rt, the reaction mixture was poured into 250 mL ice-water which was extracted with ethyl acetate (3×50 mL), washed with water (2×50 mL), brine (50 mL) and dried over $Na_2SO_4$. After removal of solvent, the residue was purified by silica gel column chromatography with ethyl acetate/hexane as eluent to give 1450 mg (75% yield) of product (10).

2-Fluoro-4-methoxy-3-(3-nitro-phenoxy)-phenyl]-(4-fluoro-phenyl)-methanone (11). To a 100 mL flask which contained a solution of 4-fluoro-benzoyl chloride (300 mg, 1.9 mmole) in nitrobenzene (1 mL) was added $AlCl_3$ (266 mg, 2 mmole) at −10° C. After stirring at 0° C. for 2 h, 1-fluoro-3-methoxy-2-(3-nitro-phenoxy)-benzene (10) (400 mg, 1.5 mmole) in nitrobenzene (1 mL) was added at rt. The reaction mixture was allowed to stir at rt for 24 hours. The reaction mixture was cooled to −10° C. and quenched with ice-water (50 mL), extracted with ethyl acetate (25 mL), washed with water (2×10 mL), $NaHCO_3$ (sat. 10 mL), brine (30 mL) and dried over $Na_2SO_4$. After removal of solvent, the crude was purified by crystallization from ether-hexane to give 470 mg (77% yield) of compound (11). LCMS: Calc. 385.3; APCI⁻ (M) 385.0: 100%

2-Fluoro-1-(4-fluoro-benzyl)-4-methoxy-3-(3-nitro-phenoxy)-benzene P-01. To a 25 mL vial which contained a mixture of 2-fluoro-4-methoxy-3-(3-nitro-phenoxy)-phenyl]-(4-fluoro-phenyl)-methanone (11) (385 mg, 1 mmole) in triethylsilane (0.5 mL) was added TFA (2.5 mL) at −10° C. The reaction mixture was allowed to warm to rt and stir at rt for 72 h. The reaction mixture was poured into 30 mL ice-water, extracted with ethyl acetate (3×30 mL), washed with sat. NaHCO3 (30 mL), water (20 mL), brine (30 mL) and dried over $Na_2SO_4$. After removal of solvent, the residue was purified by silica gel column chromatography with ethyl acetate/hexane as eluent to give 290 mg (75% yield) of product P-01. LCMS: Calc. 371.34; APCI⁻(M): 371.1, 96.6%

3-Fluoro-4-(4-fluoro-benzyl)-2-(3-nitro-phenoxy)-phenol P-13. To a 25 mL vial which contained a mixture of 2-fluoro-1-(4-fluoro-benzyl)-4-methoxy-3-(3-nitro-phenoxy)-benzene P-01 (37 mg, 0.1 mmole) in DCM (3 mL) was added $BBr_3$ (100 mg, 0.4 mmole) at −78° C. under $N_2$. The reaction mixture was stirred at −78° C. to r.t. and rt over night. The reaction mixture was diluted with water and extracted with DCM (2×10 ml). DCM layer was washed with water (2×20 ml), brine, and dried over $Na_2SO_4$. After removal of solvent, the residue was purified by silica gel column chromatography with ethyl acetate/hexane as eluent to give 27 mg (70% yield) of product P-13. LCMS: Calc. 357.3; APCI⁻(M−1) 356.0: >99%

3-[2-Fluoro-3-(4-fluoro-benzyl)-6-methoxy-phenoxy]-phenylamine P-02. To a 200 mL pressure-resistant vial which contained a mixture of 2-fluoro-1-(4-fluoro-benzyl)-4-methoxy-3-(3-nitro-phenoxy)-benzene P-01 (180 mg, 0.5 mmole) in EtOH (10 mL) was added Ranny Ni (150 mg, excess) at rt. The reaction mixture was flashed 3 times with H2 and then shacked under $H_2$ (40 psi) atmosphere for 2 h. After the catalyst was filtered out, the solvent was removed in vacuo to give 140 mg (85% yield) of desired product P-02.

2-(3-Chloro-phenoxy)-3-fluoro-4-(4-fluoro-benzyl)-1-methoxy-benzene P-03. To a 250 mL flask which contained the suspension of 3-[2-fluoro-3-(4-fluoro-benzyl)-6-methoxy-phenoxy]-phenylamine (P-02) (135 mg, 0.4 mmole) in aq HCl (12 N. 5 mL) was slowly added the solution of sodium nitrite (50 mg, 0.7 mmole) in water (3 mL) at 0° C. The mixture was allowed to stir at 0° C.-5° C. for 1 h, and then was cooled to 0° C. A solution of copper(I) chloride (55 mg, 0.4 mmol) in aq. HCl (12 N. 2 mL)) was added at 0° C. and the reaction mixture which resolved was allowed warm to rt and stir at rt for 1 h. The mixture was poured into 50 mL ice-water, extracted with ethyl acetate (3×30 mL), washed with water (2×30 mL), $NaHCO_3$ (sat. 30 mL), brine (30 mL) and dried over $Na_2SO_4$. After removal of solvent, the residue was purified by Prep TLC with ethyl acetate/Hexane as eluent to give 45 mg (33% yield) of product P-03.

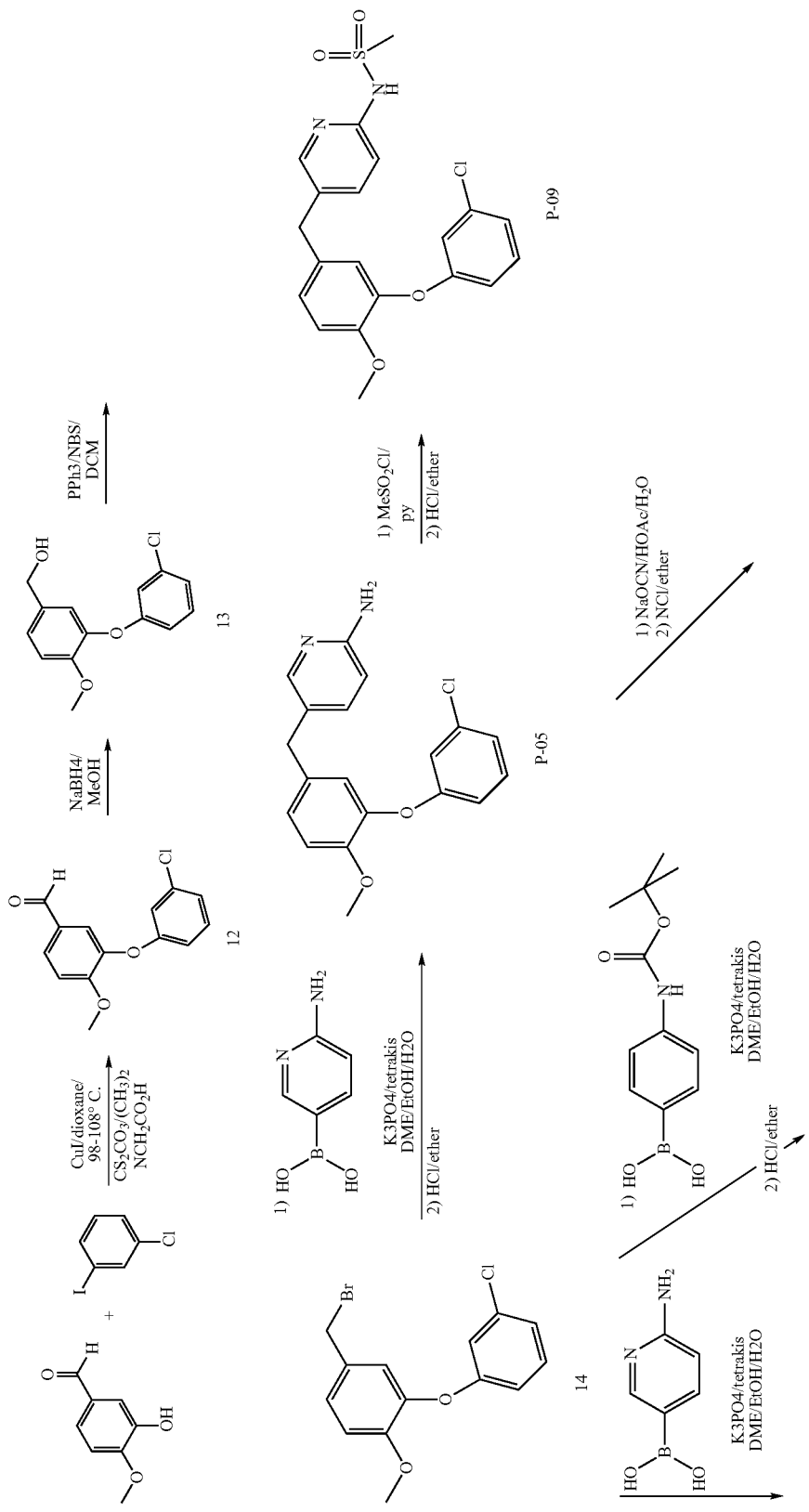

-continued
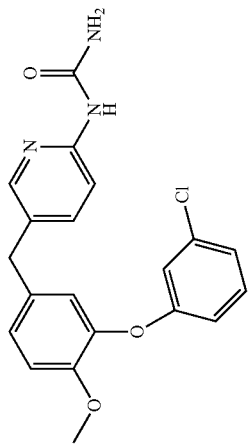
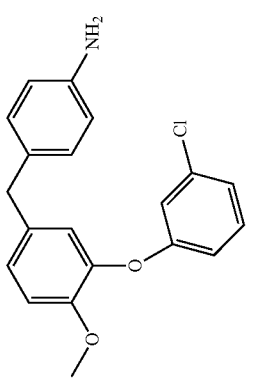
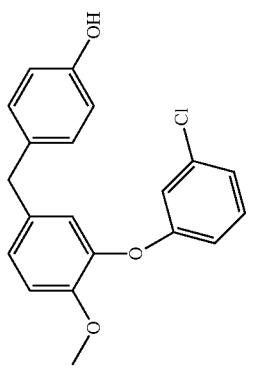
P-05
P-06
P-07
P-08
P-09

3-(3-Chloro-phenoxy)-4-methoxy-benzaldehyde (12). To a 250 mL pressure resistant vial which contained a mixture of 3-hydroxy-4-methoxy-benzaldehyde (1520 mg, 10 mmole), 1-Iodo-3-chloro-benzene (2390 mg, 10 mmole), $Cs_2CO_3$ (1600 mg, 10 mmole) and N,N-dimethylglycine.HCl (280 mg, 2 mmole) in dioxane (40 mL) was added CuI (380 mg, 2 mmole) at rt. The reaction mixture was bumbled with Ar for 5 min at rt and then the vial was sealed. The reaction mixture was heated to 98° C. and stirred for 24 h and then 110° C. for 20 h. After cooling to rt, the reaction mixture was poured onto 250 mL ice-water which was extracted with ethyl acetate (3×50 mL), washed with water (2×50 mL), brine (50 mL) and dried over $Na_2SO_4$. After removal of solvent, the residue was purified by silica gel column chromatography with ethyl acetate/hexane as eluent to give 500 mg (24% yield) of product (12).

[3-(3-Chloro-phenoxy)-4-methoxy-phenyl]-methanol (13). To a solution of 3-(3-chloro-phenoxy)-4-methoxy-benzaldehyde (12) (393 mg, 1.5 mmol) in methanol (5 ml) was added sodium borohydride (300 mg, 7 mmol) at 0° C. The reaction mixture was stirred at room temperature for 16 h. The mixture was poured into ice-water, extracted with ethyl acetate, washed with water and brine, and dried over $Na_2SO_4$. The solvent was removed under vacuum to yield 330 mg (85% yield) of compound (13).

4-Bromomethyl-2-(3-chloro-phenoxy)-1-methoxy-benzene (14). To a solution of 3-(3-chloro-phenoxy)-4-methoxy-phenyl]-methanol (13) (315 mg, 1.2 mmol) and triphenylphosphine (390 mg, 1.5 mmol) in methylene chloride (5 ml) was added NBS (0.250 mg, 1.4 mmol) in portions at 0° C. under nitrogen. After 10 min of stirring at 0° C., the mixture was allowed to warm to room temperature, and continued to stir for 16 h. After the solvent was removed, the residue was purified by silica gel column chromatography with ether/hexane as eluent to give 360 mg (85% yield) of product (14).

5-[3-(3-Chloro-phenoxy)-4-methoxy-benzyl]-pyridin-2-ylamine HCl salt P-05. A mixture of 4-bromomethyl-2-(3-chloro-phenoxy)-1-methoxy-benzene(14) (0.33 g, 1 mmol) and 2-aminopyridine-5-boronic acid pinacol (0.30 g, 1.3 mmol) in DME/EtOH/$H_2O$ (4/1/1, 12 ml) was added potassium phosphate (0.46 g, 2.2 mmol) and tetrakis(triphenylphosphine)palladium (0) (120 mg, 0.1 mmol) under nitrogen. The reaction mixture was heated to 80 C for 4 h. The reaction was diluted with water, extracted with ethyl acetate, washed with water and brine, and dried over $Na_2SO_4$. After it was concentrated in vacuo, the residue was purified by a chromatography on silica gel to yield the desired product, P-05, which using 2N HCl in ether was to convert into its HCl salt 185 mg (49% yield).

N-{5-[3-(3-Chloro-phenoxy)-4-methoxy-benzyl]-pyridin-2-yl}-methanesulfonamide HCl salt, P-09. To a 25 mL vial which contained 5-[3-(3-chloro-phenoxy)-4-methoxy-benzyl]-pyridin-2-ylamine P-05 (170 mg, 0.5 mmol) in pyridine (8 mL) was added methanesulfonyl chloride (144 mg, 1.3 mmol) at rt. The mixture was stirred at rt for 24 h. The mixture was poured into 50 mL ice-water and extracted with ethyl acetate, washed with water 1 N HCl, brine, and dried over $Na_2SO_4$. After it was concentrated in vacuo, the residue was purified by chromatography on silica gel with ethyl acetate/hexane as eluent to yield 80 mg (38% yield) of the desired product, P-09, using 2N HCl in ether was to convert into its HCl salt 50 mg (60% yield).

{5-[3-(3-Chloro-phenoxy)-4-methoxy-benzyl]-pyridin-2-yl}-urea HCl salt, P-06. To a 25 mL vial which contained 5-[3-(3-chloro-phenoxy)-4-methoxy-benzyl]-pyridin-2-ylamine P-05 (52 mg, 0.15 mmol) in HOAc-$H_2O$ (1:2, 3 mL) was added sodium cyanate (52 mg, 0.9 mmol) at rt. The vial was sealed and the reaction mixture was heated and stirred at 60° C. for 6 h. The mixture was poured into 20 mL ice-water and the solid which formed was filtered out, washed with water, dried over air to afford 45 mg (77% yield) of the desired urea, P-06, which using 2N HCl in ether was to convert into its HCl salt 35 mg (70% yield).

4-[3-(3-chloro-phenoxy)-4-methoxy-benzyl]-phenol, P-08. A mixture of 4-bromomethyl-2-(3-chloro-phenoxy)-1-methoxy-benzene (14) (0.33 g, 1 mmol) and 4-hydroxyphenyl-boronic acid (0.31 g, 2.5 mmol) in DME/EtOH/$H_2O$ (4/1/1, 12 ml) was added potassium phosphate (0.46 g, 2.2 mmol) and tetrakis(triphenylphosphine) palladium (0) (120 mg, 0.1 mmol) under nitrogen. The reaction mixture was heated to 80 C for 4 h. The reaction was diluted with water, extracted with ethyl acetate, washed with water and brine, and dried over $Na_2SO_4$. After it was concentrated in vacuo, the residue was purified by a chromatography on silica gel to yield 80 mg (23% yiled) of the desire product P-08.

4-[3-(3-Chloro-phenoxy)-4-methoxy-benzyl]-phenylamine HCl salt, P-07. A mixture of 4-bromomethyl-2-(3-chloro-phenoxy)-1-methoxy-benzene (14) (0.33 g, 1 mmol) and 4-boc aminophenylboronic acid (0.24 g, 1.3 mmol) in DME/EtOH/$H_2O$ (4/1/1, 12 ml) was added potassium phosphate (0.46 g, 2.2 mmol) and tetrakis(triphenylphosphine) palladium (0) (120 mg, 0.1 mmol) under nitrogen. The reaction mixture was heated to 80 C for 4 h. The reaction was diluted with water, extracted with ethyl acetate, washed with water and brine, and dried over $Na_2SO_4$. After it was concentrated in vacuo, the residue was purified by chromatography on silica gel to yield 80 mg (20%) of the N-Boc protected intermediate. N-Boc de-protection and subsequent formation of HCl salt was obtained using 2N HCl in ether. The desired product P-07 was obtained in 60 mg (70% yield) as HCl salt.

Scheme 7:

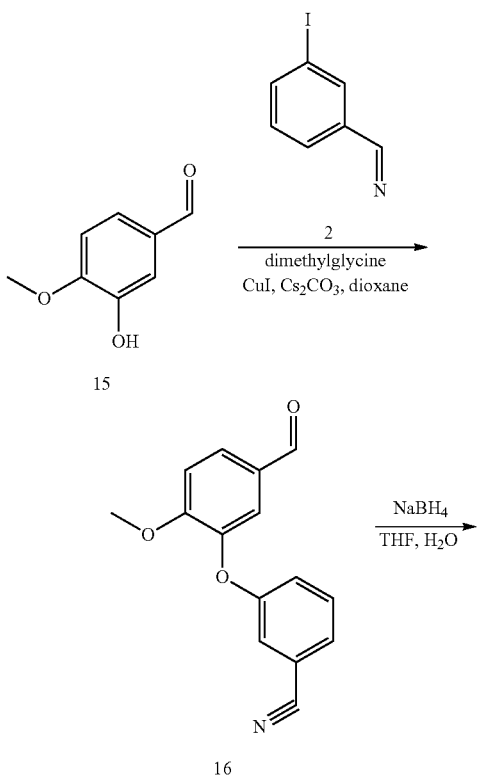

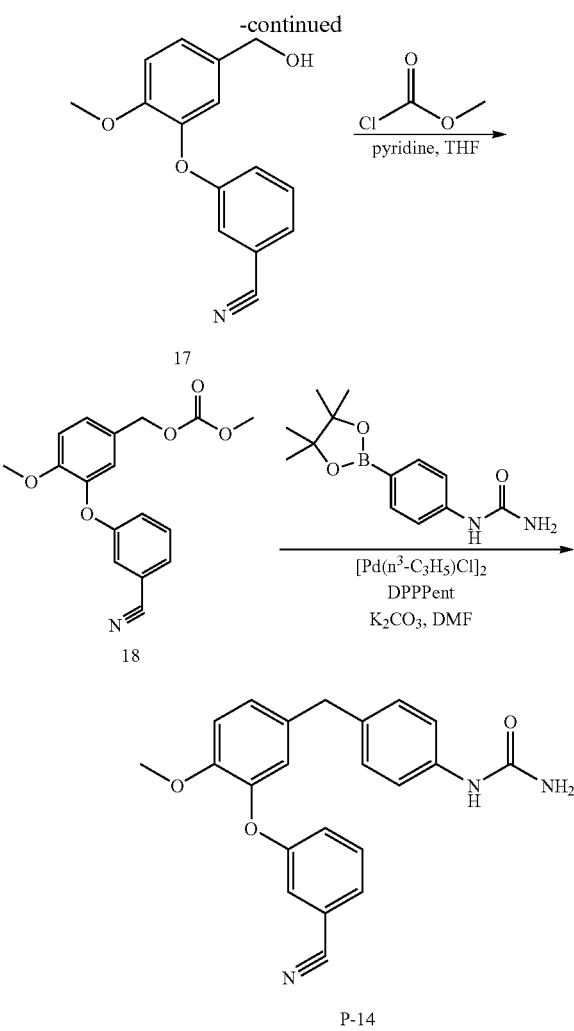

3-(5-Formyl-2-methoxy-phenoxy)-benzonitrile (16): In a 350 mL pressure vessel equipped with a stir bar was placed 3-hydroxy-4-methoxy-benzaldehyde (15) (1.5 g, 9.86 mmol), 3-iodo-benzonitrile (3.39 g, 14.8 mmol), cesium carbonate (3.21 g, 9.86 mmol), N,N-dimethylglycine (275 mg, 1.97 mmol), copper(I) iodide (188 mg, 0.986 mmol) and 1,4-dioxane (55 mL). The mixture was heated to 100° C. for 46 hours. The reaction was cooled to room temperature, quenched with water (300 mL) and then extracted with ethyl acetate (3×200 mL). The organic portions were combined, washed with brine (300 mL), dried ($MgSO_4$) and concentrated. The crude material was purified by silica gel column chromatography utilizing 35%, 50%, 75% ethyl acetate/hexanes to produce 1.09 g (42% yield) of (16) as a white solid.

3-(5-Hydroxymethyl-2-methoxy-phenoxy)-benzonitrile (17): In a 40 mL vial equipped with a stir bar was placed (16) (1.09 g, 4.27 mmol), tetrahydrofuran (10 mL), water (10 mL) and sodium borohydride (485 mg, 12.8 mmol). The mixture was stirred at room temperature for 2 hours and then quenched with water (60 mL). After extractions with ethyl acetate (3×50 mL), the organic portions were combined, washed with brine (75 mL), dried ($MgSO_4$), concentrated. The resulting solid was dried in a high vacuum oven for 5 hours at 45° C. and 945 mg (86% yield) of (17) was isolated.

Carbonic acid 3-(3-cyano-phenoxy)-4-methoxy-benzyl ester methyl ester (18): In an 40 mL vial equipped with a stir bar was placed (17) (940 mg, 3.68 mmol), anhydrous tetrahydrofuran (18 mL) and pyridine (774 µL, 9.57 mmol). The resulting clear solution was cooled in an ice water bath for 10 minutes and then methyl chloroformate (626 µL, 8.10 mmol) was added and reaction mixture was slowly warmed to room temperature and reacted for 16 hours. The reaction was concentrated by a stream of nitrogen followed by treatment with water (50 mL) and 1M HCl (40 mL). The aqueous portion was extracted with dichloromethane (3×50 mL). The organic portions were combined, washed with brine (50 mL), dried ($MgSO_4$) and concentrated to produce 1.09 g (95% yield) of (18) as a colorless, viscous oil.

{4-[3-(3-Cyano-phenoxy)-4-methoxy-benzyl]-phenyl}-urea P-14: In an 8 mL vial equipped with a stir bar was placed (18) (150 mg, 0.479 mmol), [4-(4,4,5,5-tetramethyl-[1,3,2]dioxaborolan-2-yl)-phenyl]-urea (138 mg, 0.527 mmol), potassium carbonate (199 mg, 1.44 mmol), 1,5-bis(diphenylphosphino)pentane (63.3 mg, 0.144 mmol), and dimethylformamide (2.5 mL). The mixture was degassed with nitrogen for 15 minutes and then allylpalladium(II) chloride dimer (26.3 mg, 0.0719 mmol) was added. The mixture was heated to 85° C. for 19 hours. The reaction mixture was filtered through celite and to the filtrate were added water (30 mL) and saturated ammonium chloride solution (30 mL). After extractions with ethyl acetate (2×35 mL), the organic portions were combined, washed with brine (30 mL), dried ($MgSO_4$) and concentrated. The crude material was purified by silica gel column chromatography utilizing 30% acetone/DCM as the eluent to produce 77 mg (43% yield) of P-14 as a pale orange solid. MS (APCI+): 374.1 (M+1).

Scheme 8:

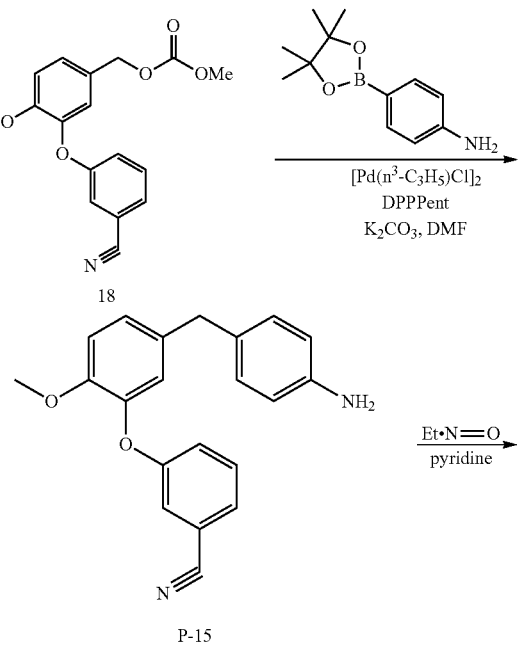

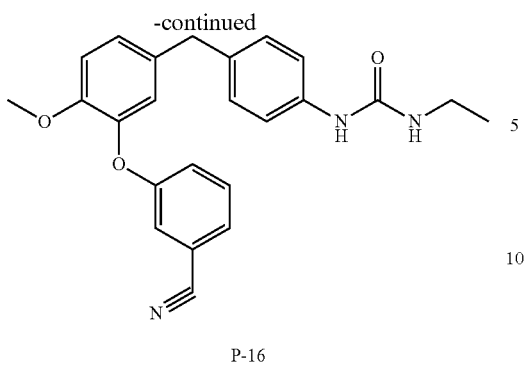

P-15
P-16

3-[5-(4-Amino-benzyl)-2-methoxy-phenoxy]-benzonitrile P-15. In an 8 mL vial equipped with a stir bar was placed (18) (250 mg, 0.798 mmol), 4-(4,4,5,5-tetramethyl-[1,3,2]dioxaborolan-2-yl)-phenylamine (192 mg, 0.878 mmol), potassium carbonate (331 mg, 2.39 mmol), 1,5-bis(diphenylphosphino)pentane (105 mg, 0.239 mmol), and dimethylformamide (4.5 mL). The mixture was degassed with nitrogen for 15 minutes and allylpalladium(II) chloride dimer (43.8 mg, 0.120 mmol) was added. The mixture was heated to 85° C. for 18 hours. The reaction mixture was filtered through celite and to the filtrate were added water (30 mL) and saturated ammonium chloride solution (30 mL). After extractions with ethyl acetate (2×75 mL), the organic portions were combined, washed with brine (50 mL), dried (MgSO$_4$) and concentrated. The crude material was purified by silica gel column chromatography utilizing 50% ethyl acetate/hexanes to produce 118 mg (45% yield) of P-15 as a yellow viscous oil. MS (APCI+): 331.1 (M+1), LC-MS: >99%

1-{4-[3-(3-Cyano-phenoxy)-4-methoxy-benzyl]-phenyl}-3-ethyl-urea P-16. In an 8 mL vial equipped with a stir bar was placed P-15 (60 mg, 0.182 mmol), pyridine (750 µL) and ethyl isocyanate (115 µL, 1.46 mmol). The mixture was stirred for 16 hours at room temperature and then treated with water (6 mL). After stirring for 45 minutes, the solid was collected, washed with water (3×3 mL) and dried in a high vacuum oven for 5 hours at 45° C. to produce 60 mg (82% yield) of P-16 as a white solid in. MS (APCI+): 402.1 (M+1) LC-MS: 99%

TABLE 1

List of Specific Examples

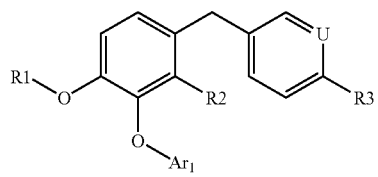

| Example No | R1 | R2 | Ar1 | U | R3 |
|---|---|---|---|---|---|
| P-01 | CH$_3$ | F | 3-NO$_2$ phenyl | CH | F |
| P-02 | CH$_3$ | F | 3-NH$_2$ phenyl | CH | F |
| P-03 | CH$_3$ | F | 3-Cl phenyl | CH | F |
| P-04 | CH$_3$ | H | phenyl | CH | NH—SO$_2$—CH$_3$ |
| P-05 | CH$_3$ | H | 3-Cl phenyl | N | NH$_2$ |
| P-06 | CH$_3$ | H | 3-Cl phenyl | N | NH—CO—NH$_2$ |
| P-07 | CH$_3$ | H | 3-Cl phenyl | CH | NH$_2$ |
| P-08 | CH$_3$ | H | 3-Cl phenyl | CH | OH |
| P-09 | CH$_3$ | H | 3-Cl phenyl | N | NH—SO$_2$CH$_3$ |

TABLE 1-continued

List of Specific Examples

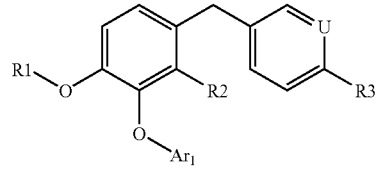

| Example No | R1 | R2 | Ar1 | U | R3 |
|---|---|---|---|---|---|
| P-10 | CH$_3$ | F | 4-F phenyl | CH | NH—CO—NH$_2$ |
| P-11 | CH$_3$ | F | 4-F phenyl | CH | NH—CO—NH$_2$ |
| P-12 | CH$_3$ | F | Ar1 = 2-pyridyl | CH | NH—CO—NH$_2$ |
| P-13 | H | F | 3-NO$_2$ phenyl | CH | F |
| P-14 | CH$_3$ | H | 3-CN phenyl | CH | NH—CO—NH$_2$ |
| P-15 | CH$_3$ | H | 3-CN phenyl | CH | NH$_2$ |
| P-16 | CH$_3$ | H | 3-CN phenyl | CH | NH—CO—NH-Et |

Methods of the invention parallel the compositions and formulations. The methods comprise administering to a patient in need of treatment a therapeutically effective amount of a compound according to the invention. The present invention also provides a method for inhibiting phosphodiesterase 4.

In-vitro assay for PDE4 enzymes. The in-vitro activity of PDE4 enzymes and the in-vitro potency of therapeutic agents described in the present invention was measured using a real-time, enzyme-coupled spectrophotometric assay. By using three different coupling enzymes, the product of the PDE4 reaction is coupled to the oxidation of the reduced form β-nicotinamide adenine dinucleotide (NADH), which dissipation can be monitored spectrophotmetrically at 340 nM.

Assay description. Buffer A containing 50 mM Tris, pH 8.0, 16 mM MgCl$_2$ and 80 mM KCl is prepared and stored at room temperature. Buffer B containing 50 mM Tris, pH 8.0 is prepared and stored at room temperature. Stock solutions of the following reagents are prepared in Buffer B and stored at −20° C.: Adenosine-5'-triphosphate (ATP), cyclic adenosine-5'-monophosphate (cAMP), phosphoenolpyruvate (PEP) and NADH. An assay mix is prepared by mixing Buffer A, trichloroethylphosphine (TCEP), ATP, PEP, NADH, myokinase (MK), pyruvate kinase (PK), lactate dehydroganese (LDH) and PDE4 to a final volume of 20 mL, which is enough for a single 96-well assay plate. Assay mix (180 µL) and test article (10 µL) in 1:1 DMSO/H$_2$O mixture is pre-incubated at room temperature for 10 min. The enzymatic reaction is initiated by addition of cAMP (10 µL). Final concentration of all components in the assay (200 µL/well) are as follows: 10 mM MgCl$_2$, 50 mM KCl, 5 mM TCEP, 2.5% DMSO, 0.4 mM NADH, 1 mM PEP, 0.04 mM ATP, 5 units MK, 1 unit PK, 1 unit LDH and appropriate amount of PDE4. Reaction progress curves are monitored in a plate reader capable of measuring light absorbance at 340 nM. A decrease in light absorbance at 340 nm is due to oxidation of NADH. Positive controls containing no test article and negative controls containing no test article and no cAMP are included on every assay plate. Reaction rates are determined from the slopes of the linear portions of the progress curves. All data are percent normalized with respect to controls and presented as percent inhibition.

The results of testing of representative species are shown below in Table 2

TABLE 2

| Example No | h4D7 | h4B1 |
|---|---|---|
| P-01 | A | D |
| P-02 | D | D |
| P-03 | A | B |
| P-04 | D | D |
| P-05 | B | C |
| P-06 | B | B |
| P-07 | B | B |
| P-08 | B | D |
| P-09 | B | D |
| P-10 | C | D |
| P-11 | A | B |
| P-12 | A | D |

Where: A < 1 uM, B = 1-10, C = 11-20, D > 21

The activity of PDE4 inhibitors described in the present invention was also measured using in an ex-vivo assay measuring leukotriene E4 (LTE4) in human whole blood after Sephadex stimulation. The anti-inflammatory activity of therapeutic agents of the present invention is demonstrated by the inhibition of eosinophil activation as measured by sephadex bead stimulated LTE4 production in whole human blood. For each sample, 356 µl of heparinized human whole blood (Vacutainer tube #6480) is added to wells of a 96 well plate. Then, 4 µl of a series of compound dilutions (in DMSO) are added in triplicates, suspension mixed and allowed to incubate at 37° C. for 15 min with gentle shaking. After that, blood samples are stimulated by adding 40 µL of Sephadex G-15 beads (Sigma-Aldrich, Sweden). The beads are predissolved in PBS (0.16 g/mL PBS). After mixing, the suspension is incubated at 37° C. for 90 min. Then, 8 µL of 15% EDTA/PBS is added to each sample, mixed and plate centrifuged for 5 min at 115×g at 21° C. and supernatants taken. In each plate, 10 positive controls and 10 negative controls are used, containing DMSO instead of compound solution. The positive controls are stimulated with Sephadex as described for the samples, and in the negative controls (unstimulated), Sephadex solution is replaced by PBS. $LTE_4$ levels in the resulting plasma samples are determined using a commercial enzyme-linked immunoassay (Cayman Chemical Company, Ann Arbor, Mich.) according to the manufacturer's instructions. A representative example, example P-01, showed IC50<1 µM in this ex-vivo assay. Persons of skill in the art accept that positive results in PDE4 models are predictive of therapeutic utility as discussed above.

We claim:
1. A compound of formula I:

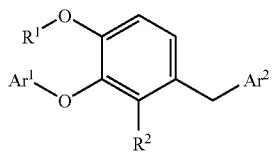

or a salt thereof, wherein:
$R^1$ is chosen from H, $(C_1-C_8)$alkyl and halo$(C_1-C_8)$alkyl;
$R^2$ is chosen from H and halo;
$Ar^1$ is selected from optionally substituted phenyl and optionally substituted heteroaryl, wherein substituted phenyl and substituted heteroaryl refer to phenyl and heteroaryl residues wherein up to three H atoms in each residue are individually replaced with halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), or —NHSO$_2$NH$_2$ ; and
$Ar^2$ is selected from:
(a) phenyl substituted in the para position with a single substituent selected from halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), and —NHSO$_2$NH$_2$; and
(b) pyridinyl substituted in the para position with a single substituent selected from halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl) aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), and —NHSO$_2$NH$_2$.

2. A compound or salt according to claim 1 wherein $Ar^2$ is phenyl substituted in the para position with a group chosen from halogen, nitro, cyano, urea, alkylurea, hydroxy, alkylsulfonylamino, amino, haloalkyl, loweralkoxy, carboxy, alkoxycarbonyl, alkylaminocarbonyl, alkylamino, dialkylamino, mercapto, alkylthio, alkylsulfoxide, alkylsulfone, acylamino, phenyl and benzyl.

3. A compound or salt according to claim 2 wherein $Ar^2$ is phenyl substituted in the para position with a group chosen from halogen, urea, alkylurea, hydroxy, alkylsulfonylamino and amino.

4. A compound or salt according to claim 1 wherein $Ar^2$ is 3-pyridinyl substituted in the 6-position with a group chosen from halogen, nitro, cyano, urea, sulfonylurea, hydroxy, alkylsulfonylamino, amino, haloalkyl, loweralkoxy, carboxy, alkoxycarbonyl, alkylaminocarbonyl, alkylamino, dialkylamino, mercapto, alkylthio, alkylsulfoxide, alkylsulfone, acylamino, phenyl and benzyl.

5. A compound or salt according to claim 4 wherein Ar² is 3-pyridinyl substituted in the 6-position with a group chosen from urea, alkylsulfonylamino and amino.

6. A compound or salt according to claim 1 wherein R² is hydrogen.

7. A compound or salt according to claim 1 wherein R² is fluorine.

8. A compound of formula I:

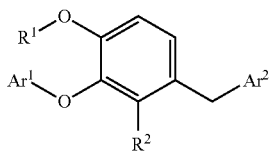

or a salt thereof wherein:
R¹ is hydrogen;
R² is chosen from hydrogen and halo;
Ar¹ is selected from optionally substituted phenyl and optionally substituted heteroaryl; and
Ar² is selected from substituted phenyl and substituted heteroaryl,
wherein substituted phenyl and substituted heteroaryl refer to phenyl and heteroaryl residues wherein up to three H atoms in each residue are individually replaced with halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), or —NHSO₂NH₂;
with the proviso that when R¹ and R² are both H, Ar² is not phenyl having substituents at the 2- and 6-positions.

9. A compound or salt according to claim 1 wherein R¹ is methyl.

10. A compound of formula I:

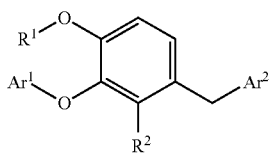

or a salt thereof wherein
(a) R¹ is hydrogen or methyl;
(b) R² is hydrogen or fluorine;

(c) Ar¹ is chosen from
(i) phenyl;
(ii) phenyl substituted in the meta or para position with a group chosen from halogen, nitro, cyano, trifluoromethyl and amino; and
(iii) pyridinyl; and
(d) Ar² is chosen from
(i) phenyl substituted in the para position with a substituent selected from halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), and —NHSO₂NH₂; and
(ii) 3-pyridinyl substituted in the 6-position with a substituent selected from halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), and —NHSO₂NH₂.

11. A salt of a compound of claim 8 wherein the salt is a pharmaceutically acceptable salt.

12. A pharmaceutical composition comprising a pharmaceutically acceptable carrier and a compound or pharmaceutically acceptable salt according to claim 8.

13. A pharmaceutical composition comprising
(a) a pharmaceutically acceptable carrier;
(b) a compound formula I:

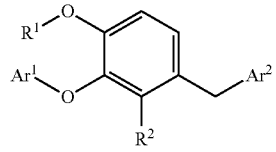

or a pharmaceutically acceptable salt thereof, wherein
R¹ is chosen from H, (C₁-C₈)alkyl and halo(C₁-C₈)alkyl;
R² is chosen from H and halo;
Ar¹ is selected from optionally substituted phenyl and optionally substituted heteroaryl; and Ar² is selected from substituted phenyl and substituted heteroaryl;

with the provisos that
(1) when R¹ and R² are both H, Ar² is not phenyl having substituents at the 2- and 6-positions; and
(2) when R¹ is CH₃ and R² is H, Ar$^e$ is not 2,4-diaminopyrimidin-5-yl, wherein substituted phenyl and substituted heteroaryl refer to phenyl and heteroaryl residues wherein up to three H atoms in each residue are replaced with halogen, alkyl, haloalkyl, haloalkoxy, hydroxy, loweralkoxy, oxaalkyl, carboxy, carboalkoxy, carboxamido, alkylaminocarbonyl, alkoxycarbonyl, alkoxycarbonylamino, acyl, alkoxyalkyl, benzenesulfonyl, cyano, carbonyl, nitro, amino, urea, alkylurea, hydroxyalkyl, alkylamino, dialkylamino, aminoalkyl, (alkyl)(aryl)aminoalkyl, alkylaminoalkyl, dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, acetoxy, sulfoxide, alkylsulfoxide, sulfone, alkylsulfone, sulfonylamino, alkylsulfonylamino, aryl, heterocyclyl, hydroxyimino, alkoxyimino, aminosulfonyl, trityl, amidino, guanidino, ureido, benzyloxyphenyl, benzyl, heteroaryl, heterocyclylalkyl, phenoxy, benzyloxy, heteroaryloxy, —NH(tBoc), or —NHSO₂NH₂; and (c) a second agent chosen from cholinesterase inhibitors, NMDA antagonists, calpain inhibitors and antioxidants.

14. A pharmaceutical composition according to claim 13 wherein said second agent is chosen from tacrine, huperzine, donepezil, lanicemine, remacemide, neramexane, memantine, vitamin E and coenzyme Q10.

15. A compound or salt according to claim 1 wherein Ar¹ is selected from:
(a) phenyl;
(b) phenyl substituted in the meta or para position with a single substituent; and
(c) pyridinyl.

16. A compound or salt according to claim 15 wherein Ar¹ is phenyl substituted in the meta or para position with a group chosen from halogen, nitro, cyano, fluoromethyl and amino.

17. A compound or salt according to claim 1 wherein
(a) R¹ is hydrogen or methyl;
(b) R² is hydrogen or fluorine;
(c) Ar¹ is chosen from
  (i) phenyl;
  (ii) phenyl substituted in the meta or para position with a group chosen from halogen, nitro, cyano, trifluoromethyl and amino; and
  (iii) pyridinyl; and
(d) Ar$^e$ is chosen from
  (i) phenyl substituted in the para position; and
  (ii) 3-pyridinyl substituted in the 6-position.

18. A salt of a compound of claim 1 wherein the salt is a pharmaceutically acceptable salt.

19. A pharmaceutical composition comprising a pharmaceutically acceptable carrier and a compound or pharmaceutically acceptable salt according to claim 1.

20. A salt of a compound of claim 8 wherein the salt is a pharmaceutically acceptable salt.

21. A pharmaceutical composition comprising a pharmaceutically acceptable carrier and a compound or pharmaceutically acceptable salt according to claim 10.

22. A compound or salt according to claim 8 wherein Ar² is selected from substituted phenyl and substituted monocyclic heteroaryl.

23. A compound or salt according to claim 8 wherein Ar¹ is selected from:
(a) phenyl;
(b) phenyl substituted in the meta or para position with a single substituent; and
(c) pyridinyl.

24. A compound or salt according to claim 23 wherein Ar¹ is phenyl substituted in the meta or para position with a group chosen from halogen, nitro, cyano, fluoromethyl and amino.

25. A compound or salt according to claim 8 wherein R² is hydrogen.

26. A compound or salt according to claim 8 wherein R² is fluorine.

27. A pharmaceutical composition according to claim 13 wherein Ar² is selected from substituted phenyl and substituted monocyclic heteroaryl.

28. A pharmaceutical composition according to claim 13 wherein Ar¹ is selected from:
(a) phenyl;
(b) phenyl substituted in the meta or para position with a single substituent; and
(c) pyridinyl.

29. A pharmaceutical composition according to claim 13 wherein Ar¹ is phenyl substituted in the meta or para position with a group chosen from halogen, nitro, cyano, fluoromethyl and amino.

* * * * *

UNITED STATES PATENT AND TRADEMARK OFFICE
CERTIFICATE OF CORRECTION

PATENT NO.         : 8,877,816 B2                                        Page 1 of 1
APPLICATION NO.    : 12/275168
DATED              : November 4, 2014
INVENTOR(S)        : Singh et al.

It is certified that error appears in the above-identified patent and that said Letters Patent is hereby corrected as shown below:

In the Claims,

Column 37, Line 6: Claim 13, Delete "is H, $Ar^e$ is" and insert -- is H, $Ar^2$ is --

Column 38, Line 7: Claim 17, Delete "(d) $Ar^e$" and insert -- (d) $Ar^2$ --

Column 38, Line 15: Claim 20, Delete "claim 8" and insert -- claim 10 --

Signed and Sealed this
Twenty-fourth Day of March, 2015

Michelle K. Lee
*Director of the United States Patent and Trademark Office*